(12) United States Patent
Kim et al.

(10) Patent No.: US 10,202,476 B2
(45) Date of Patent: Feb. 12, 2019

(54) POLYBUTENE PREPARATION METHOD

(71) Applicant: DAELIM INDUSTRIAL CO., LTD., Seoul (KR)

(72) Inventors: Myeong Seok Kim, Daejeon (KR); Min Sup Park, Daejeon (KR); Hyung Jae Seo, Daejeon (KR); Se Hyun Lee, Daejeon (KR)

(73) Assignee: DAELIM INDUSTRIAL CO., LTD., Seoul (KR)

( * ) Notice: Subject to any disclaimer, the term of this patent is extended or adjusted under 35 U.S.C. 154(b) by 0 days.

(21) Appl. No.: 15/505,322

(22) PCT Filed: Aug. 21, 2015

(86) PCT No.: PCT/KR2015/008776
§ 371 (c)(1),
(2) Date: Feb. 21, 2017

(87) PCT Pub. No.: WO2016/028123
PCT Pub. Date: Feb. 25, 2016

(65) Prior Publication Data
US 2017/0267795 A1    Sep. 21, 2017

(30) Foreign Application Priority Data

Aug. 22, 2014 (KR) .................. 10-2014-0109548

(51) Int. Cl.
*C08F 210/10* (2006.01)
*C08F 110/10* (2006.01)
(Continued)

(52) U.S. Cl.
CPC ........... *C08F 210/10* (2013.01); *B01J 8/0419* (2013.01); *B01J 19/245* (2013.01); *C07C 5/2556* (2013.01);
(Continued)

(58) Field of Classification Search
CPC ...... C07C 5/2556; C07C 5/277; B01J 19/245; C08F 210/10; C08F 110/10
(Continued)

(56) References Cited

U.S. PATENT DOCUMENTS 5,981,818 A    11/1999   Purvis et al.
6,137,023 A *  10/2000   Dorbon ................. C07C 5/2791
                                                              203/28
(Continued)

FOREIGN PATENT DOCUMENTS

CN           1395582        2/2003
JP       H10231256 B2       9/1998
(Continued)

OTHER PUBLICATIONS

Online machine translation of KR 10-0851639; publication date: Aug. 5, 2008.*
(Continued)

*Primary Examiner* — Fred M Teskin
(74) *Attorney, Agent, or Firm* — Nath, Goldberg & Meyer; Tanya E. Harkins; Joshua B. Goldberg (57) ABSTRACT

A method for preparing polybutene includes the steps of: supplying a C4 mixture to an isomerization reactor in which (i) 1-butene is isomerized into 2-butene by a hydrogen isomerization reaction using an isomerization catalyst in an isomerization zone of the isomerization reactor and (ii) iso-butene and 2-butene are separated by fractional distillation in a fractional distillation zone; supplying a C4 mixture containing 2-butene which is separated in the isomerization reactor to a skeletal isomerization reactor, in which a part of normal-butene is skeletal isomerized into iso-butene by a skeletal isomerization reaction using a skeletal isomerization catalyst, and the obtained skeletal isomerization mixture is supplied and recycled to the isomerization reactor; and
(Continued)

supplying (i) a raw material containing the iso-butene of high concentration and which is separated from the isomerization reactor and (ii) a polymerization catalyst to a polybutene polymerization reactor and thereby producing polybutene by a polymerization reaction.

12 Claims, 1 Drawing Sheet (51) Int. Cl.
*B01J 19/24* (2006.01)
*B01J 8/04* (2006.01)
*C07C 5/25* (2006.01)
*C07C 5/27* (2006.01)
*C08F 4/14* (2006.01)

(52) U.S. Cl.
CPC .......... *C07C 5/2708* (2013.01); *C07C 5/2775* (2013.01); *C08F 110/10* (2013.01); *B01J 2219/24* (2013.01); *C07C 2521/04* (2013.01); *C07C 2523/42* (2013.01); *C07C 2529/06* (2013.01); *Y02P 20/584* (2015.11)

(58) Field of Classification Search
USPC ................................ 526/348.7; 585/329, 518
See application file for complete search history.

(56) References Cited

U.S. PATENT DOCUMENTS

| 6,207,115 B1 | 3/2001 | Chodorge et al. |
| 2006/0195000 A1 | 8/2006 | Yun et al. |
| 2007/0155930 A1* | 7/2007 | Rath .................. C08F 8/26 526/348.7 |
| 2008/0214762 A1 | 9/2008 | Bode et al. |
| 2010/0234542 A1 | 9/2010 | Blackborow et al. |

FOREIGN PATENT DOCUMENTS

| JP | 2002220411 A | 8/2002 |
| KR | 1019930006910 B1 | 7/1993 |
| KR | 100851639 B1 | 8/2008 |
| KR | 1020120096389 A | 8/2012 |

OTHER PUBLICATIONS

International Search Report dated Dec. 9, 2015 corresponding to International application No. PCT/KR2015/008776.
"Applied industrial catalysis (the 1st volume)", Edited by Bruce E Leach, Translated by Zhu Hongfa, Tingjiagong publisher, Mar. 1990, Beijing.

* cited by examiner

POLYBUTENE PREPARATION METHOD

TECHNICAL FIELD

The present invention relates to a method for preparing polybutene, and more particularly, to a method for preparing polybutene in which iso-butene in a C4 mixture is very effectively utilized, thereby polybutene productivity is more improved in comparison with a conventional method for preparing polybutene by using a conventional C4 mixture.

BACKGROUND ART

Polybutene is generally prepared by polymerizing olefin components having a carbon atom number of 4 (C4), which are produced during a hydrocarbon degrading process, using a Friedel-Craft type catalyst and has a number average molecular weight (Mn) of about 300 to 5,000. When 1,3-butadiene is extracted from the C4-hydrocarbon materials which are produced in petroleum refining process (cracking of heavy oil) or Naphtha Cracking Center (NCC), the remaining raw material includes paraffins such as iso-butane, normal-butane(n-butane) and olefins such as 1-butene, 2-butene, and iso-butene. Among these, the iso-butene amount is about 20 to 50 weight %. The iso-butene is mostly used for preparation of polybutene or methyl-t-butyl ether (MTBE) which is used as an octane number enhancer. Since iso-butene, among the olefin components of C4, has the highest reactivity, the produced polybutene is mostly composed of the iso-butene unit. Further, iso-butene is used in the fields of petrochemical and specialty chemicals. Specifically, iso-butene is used to prepare ETB (Ethylene Glycol mono-t-butyl Ether), DETB (Diethylene Glycol mono-t-butyl Ether) which is a raw material for manufacturing an electronic cleaning agent, DIB (Diiso-butene), and IIR (Isobutylene Isoprene Rubber).

However, due to the recent development of shale gas, C2 hydrocarbons (ethylene, etc.) or C3 hydrocarbons (propylene, etc.) which was obtained from naphtha pyrolysis process, are being supplied at a low price. Due to this, the pyrolysis step (process) of naphtha loses competitiveness, and the naphtha cracking business is shrinking and the supply of iso-butene is decreased. So the price of iso-butene is increasing. Therefore, there is a demand for developing a method for efficiently utilizing or increasing iso-butene.

Meanwhile, in a C4 fraction produced during the catalytic cracking of heavy oil in an oil-refining process and in a C4 raffinate generated in a naphtha pyrolysis process, about 20 to 35% of 1-butene is included. The 1-butene deteriorates the productivity of polybutene, which makes it difficult to produce polybutene of high quality (high vinylidene amount and low halogen amount). In the past, since polybutene was mainly used for preparing adhesive, glue or insulating oil, conventional polybutene (Con.PB), which is not highly reactive, was mainly used. However, recently, a polar group is introduced into the polybutene so that the polybutene can be used for preparing an anti-scuff agent of engine oil, a viscosity index improver or a detergent. Therefore, the demand for high reactive polybutene (NRPB) is increasing.

One of the well-known products having the polar group is poly isobutenyl succinic anhydride (PIBSA) which is prepared by reacting polybutene with maleic anhydride. Most of fuel detergents or lubricating oil additives are prepared by using the PIBSA. The highly reactive polybutene in which the double bond of polybutene is located at the end of polybutene reacts directly with maleic anhydride, resulting in a high yield of PIBSA. On the other hand, in the case of a conventional polybutene in which the double bond is located in the interior of the polybutene, and in particular, the number of the alkyl groups substituted to the double bond is large, the reactivity of the polybutene is low due to steric hindrance. After chlorinating the polybutene with chlorine gas, PIBSA is prepared by reacting the chlorinated polybutene with maleic anhydride.

One way to increase the reactivity of polybutene is to locate the double bond at the end of the molecule to form a vinylidene group. Polybutene having a vinylidene amount of more than 70 mol % (that is, the number of vinylidene groups with respect to the total number of double bonds is 70%) is referred to a highly reactive polybutene. Polybutene having a vinylidene amount of 40 to 70 mol % is referred to a mid-reactive polybutene (MVPB, Mid Vinylidene Polybutene). Polybutene having a vinylidene amount of less than 40 mol % is referred to a low reactive polybutene. For production of highly reactive polybutene, generally, boron trifluoride ($BF_3$) is used as a catalyst, and alcohols, ethers and the like are used as co-catalysts. Further, in the case of conventional polybutene (mid-reactive and low reactive polybutene), an aluminum trichloride ($AlCl_3$) catalyst is generally used, which does not induce the double bond formation at terminal positions of the polybutene.

In both of the conventional polybutene and the highly reactive polybutene, product quality, productivity per unit catalyst, and productivity per unit raw material may be deteriorated due to normal-butene in the raw materials. The higher the iso-butene amount in the raw material, the better the product quality, the productivity per unit raw material, and the productivity per unit catalyst. It is preferable to increase the iso-butene amount in the raw material so as to increase the amount of vinylidene in the produced polybutene. The highly reactive polybutene having a high vinylidene amount can produce a high-quality product such as a lubricating oil and a fuel detergent. It is also preferable to reduce the fluoride amount in the produced polybutene. The fluoride is generated from the catalyst, and the halogen component may induce a corrosion of the reactor for preparing the detergents and the lubricants. To increase the productivity per raw material, to increase productivity per catalyst, or to decrease the chlorine amount in the product, it is preferable to increase the iso-butene amount in the raw material.

For removing 1-butene which has the greatest influence on the quality of polybutene, U.S. Pat. No. 5,674,955 discloses a method for producing a polybutene by using a raw material containing at least 5% of 1-butene and by reducing the 1-butene amount in the initial raw material to 20% or less through pretreatment of the raw material under the condition of using a halogen compound catalyst and that thereby it is possible to manufacture polybutene containing a high vinylidene amount and a low halogen amount. Further, U.S. Pat. No. 6,207,115 discloses the selective hydrogenation of a diolefin (butadiene, etc.) using an olefin conversion unit (OCU) and isomerization of 1-butene to 2-butene at the same time. Among the initial raw materials, 1-butene and iso-butene are difficult to separate due to their similar boiling points, but raw materials after isomerization can be easily separated into iso-butene and 2-butene using the difference in boiling point. In the case of general OCU, 2-butene separated at the bottom of the distillation column is relatively high in boiling point, so it is used to prepare propylene by reacting with ethylene and iso-butene separated at the upper part of the distillation column because of relatively low boiling point is used for producing polybutene.

On the other hand, to prepare high purity iso-butene, iso-butene may be separated from C4 mixture. For example, t-butyl alcohol (TBA) dehydration method combining a hydration reaction and a dehydration reaction, methyl t-butyl ether (MTBE) cracking method in which methanol is added to iso-butene using an acid catalyst and then cracked to obtain iso-butene and dehydrogenation of isobutane and so on are well known, however, all of them are expensive, and the price of polybutene is increased.

DISCLOSURE

Technical Problem

An object of the present invention is to provide a method for preparing polybutene which can reduce the production cost and increase the production amount of polybutene by effectively utilizing or increasing the amount of iso-butene in a raw material for preparing polybutene.

Another object of the present invention is to provide a method for preparing polybutene which can produce not only a highly reactive polybutene having a high amount of vinylidene and a small amount of halogen component but also a conventional polybutene having a low amount of halogen component.

Technical Solution

To achieve these objects, the present invention provides a method for preparing polybutene, comprising the steps of: supplying a C4 mixture to an isomerization reactor in which (i) 1-butene is isomerized into 2-butene by a hydrogen isomerization reaction using an isomerization catalyst in an isomerization zone of the isomerization reactor and (ii) iso-butene and 2-butene are separated by fractional distillation in a fractional distillation zone; supplying a C4 mixture containing 2-butene which is separated in the isomerization reactor to a skeletal isomerization reactor, in which a part of normal-butene is skeletal isomerized into iso-butene by a skeletal isomerization reaction using a skeletal isomerization catalyst, and the obtained skeletal isomerization mixture is supplied and recycled to the isomerization reactor; and supplying a raw material containing the iso-butene of high concentration and which is separated from the isomerization reactor and a polymerization catalyst to a polybutene polymerization reactor and thereby producing polybutene by a polymerization reaction.

Technical Effects

The preparation method of polybutene according to the present invention can increase the production amount of polybutene by more than 20% as compared with the case of using a conventional mixed C4 hydrocarbon mixture. In addition, in the present invention, since a C4 hydrocarbon mixture containing relatively high purity isobutene is used, not only highly reactive polybutene having a high vinylidene content and a low halogen content but also a conventional polybutene having a low content of halogen component can be prepared. Also, since the normal-butene is removed from the raw material, it is possible to produce a high-quality product having excellent productivity per unit raw material and productivity per unit catalyst. In addition, the catalyst mileage is improved by more than two times, and the manufacturing cost of the product can be reduced.

DETAILED DESCRIPTION OF INVENTION

Hereinafter, the present invention will be described in more detail with reference to the accompanying drawings.

Figure 1:
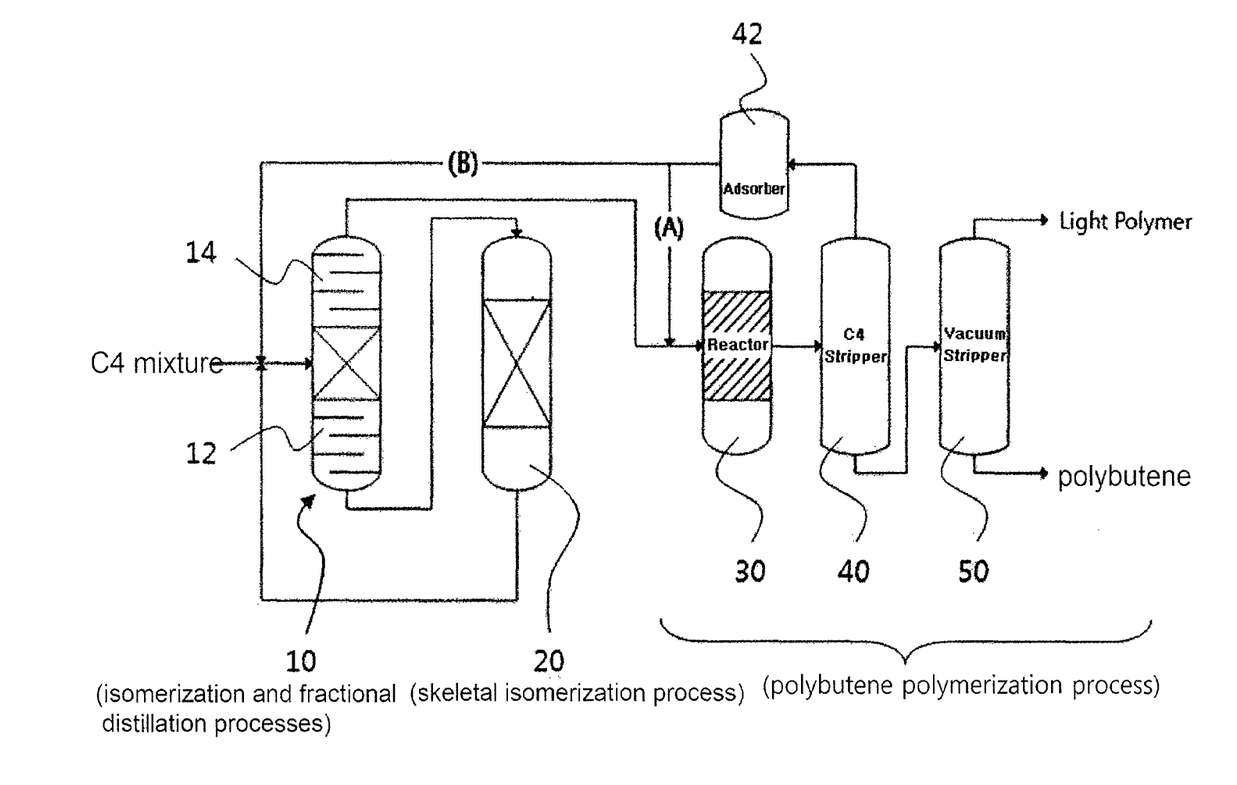
FIG. 1 is a process diagram for illustrating a method for preparing polybutene in accordance to an embodiment of the present invention.

FIG. 1 is a process diagram for illustrating a method for preparing polybutene in accordance to an embodiment of the present invention. First, as shown in FIG. 1, a C4 mixture (hydrocarbon materials having carbon atom number of 4) is supplied to an isomerization reactor 10 (or an isomerization column) and hydrogen isomerization and fractional distillation processes are performed. Specifically, at an isomerization zone 12, 1-butene is isomerized into 2-butene by a hydrogen isomerization reaction by using an isomerization catalyst. And at the same time, in a fractional distillation zone 14, iso-butene and 2-butene are separated by fractional distillation due to the difference of boiling points. When 1-butene, iso-butene, and 2-butene are mixed, their difference in boiling points is small and separation by fractional distillation is not easy. For this reason, as in the above process, before the fractional distillation, a step of isomerizing 1-butene to 2-butene is carried out, thereby avoiding the separation difficulty.

The C4 mixture can be C4-raffinate generated in a naphtha pyrolysis process or C4 fraction produced during the catalytic cracking of heavy oil in an oil-refining process. The C4 mixture may contain normal-butene of 5 weight % or more, preferably of 10 weight % or more, more preferably of 20 to 45 weight %, even more preferably of 25 to 40 weight % and iso-butene of 10 to 60 weight %, preferably of 20 to 55 weight %, more preferably of 30 to 50 weight %. For example, C4-raffinate having compositions as shown in Table 1 below or C4 fraction having the compositions shown in Table 2 below can be used. When the amount of the normal-butene contained in the C4 mixture is less than 5 weight %, the iso-butene recycling efficiency becomes about ⅛ or less, in relative to the feedstock (having at least weight 5% of normal-butene) of the following Tables 1 and 2 which are used in the present invention. Using C4 mixture having normal-butene of less than 5 weight % makes the iso-butene recycling efficiency very low, and thus the amount of iso-butene that can be obtained through the recycle process is very small, which makes it difficult to carry out the recycling process that maximizes the utilization of iso-butene through the present invention.

TABLE 1

|  | iso-butene | n-butane | 1-butene | C-2-butene | T-2-butene | i-butane |
|---|---|---|---|---|---|---|
| Amount (weight %) | 46.5 | 9.9 | 26.2 | 4.5 | 9.4 | 3.5 |

TABLE 2

|  | iso-butene | n-butane | 1-butene | C-2-butene | T-2-butene | i-butane |
|---|---|---|---|---|---|---|
| Amount (weight %) | 35.4 | 16.1 | 35.0 | 2.3 | 7.5 | 3.7 |

Further, when iso-butene and 2-butene are separated, a C4 mixture containing high concentration of iso-butene (high iso-butene concentration raw material) is discharged from the isomerization reactor (column 10) (preferably as shown in FIG. 1, the C4 mixture is discharged from the upper part of the isomerization reactor 10). The high iso-butene concentration raw material which is obtained at the isomerization reactor 10 can include iso-butene of 70 weight % or more, preferably of 80 to 98 weight %, more preferably of 85 to 95 weight %, and n-butene of 3 weight % or less, preferably of 2 weight % or less, more preferably of 0.1 to 1.5 weight %. An example of the high iso-butene concentration raw material includes a material having composition of following Table 3.

TABLE 3

| | iso-butene | n-butane | 1-butene | C-2-butene | T-2-butene | i-butane |
|---|---|---|---|---|---|---|
| Amount (weight %) | 92.9 | 0.9 | 0.6 | 0.2 | 0.3 | 5.1 |

While, when iso-butene and 2-butene are separated, a C4 mixture containing high concentration of 2-butene is discharged from the isomerization reactor (column 10) (preferably as shown in FIG. 1, the C4 mixture is discharged from the lower part of the isomerization reactor 10). The high 2-butene concentration raw material which is obtained at the isomerization reactor 10 can include 2-butene of 55 weight % or more, preferably of 60 to 90 weight %, more preferably of 65 to 80 weight %, and iso-butene of 5 weight % or less, preferably of 3 weight % or less, more preferably of 0.5 to 2 weight %. An example of the high 2-butene concentration raw material includes a material having composition of following Table 4.

TABLE 4

| | iso-butene | n-butane | 1-butene | C-2-butene | T-2-butene | i-butane |
|---|---|---|---|---|---|---|
| Amount (weight %) | 1.6 | 27.6 | 0.5 | 23.3 | 46.3 | 0.7 |

In the hydrogen isomerization reaction, the molecular formula of 1-butene is not changed, but isomerized to 2-butene by changing the position of hydrogen, that is, the position of the double bond in the molecule. The hydrogen isomerization reaction should be carried out at a temperature of 30 to 100° C., preferably 40 to 80° C., more preferably 50 to 70° C. As an isomerization catalyst used in the hydrogen isomerization reaction, a conventional acid catalyst or a base catalyst can be used, and metals such as platinum (Pt), palladium (Pd), and nickel (Ni) may also be used.

Next, a C4 mixture containing the high concentration of 2-butene which is separated in the isomerization reactor 10 is introduced into a skeletal isomerization reactor (preferably to the upper part of the skeletal isomerization reactor 20, as shown in FIG. 1). The C4 mixture may include some 1-butene which is not isomerized in the isomerization reactor 10. In the skeletal isomerization reactor 20, the n-butene is partially skeletal-isomerized into iso-butene through the skeletal isomerization reaction using a skeletal isomerization catalyst. The skeletal isomerization mixture (C4 mixture) is discharged from the skeletal isomerization reactor 20 (preferably, as shown in FIG. 1, discharged from the lower part of the skeletal isomerization reactor 20), and in turn is supplied and recycled to the isomerization reactor 10. The skeleton isomerization process is performed in this way.

The iso-butene raw material obtained in the skeletal isomerization reactor 20 may include iso-butene of 10 to 60 weight %, preferably of 20 to 50 weight %, more preferably of 25 to 40 weight % and n-butene of 20 to 53 weight %, preferably of 30 to 50 weight %, more preferably of 35 to 45 weight %. An example of a skeletal isomerization mixture obtained from the skeletal isomerization reactor 20 includes a material having composition of the following Table 5.

TABLE 5

| | iso-butene | n-butane | 1-butene | C-2-butene | T-2-butene | i-butane |
|---|---|---|---|---|---|---|
| Amount (weight %) | 29.5 | 29.1 | 10.5 | 10.5 | 19.7 | 0.7 |

The skeletal isomerization reaction refers to a conversion between a normal-form and an iso-form, preferably a conversion from a normal-form to an iso-form, wherein its molecular formula is unchanged but the structure of the carbon skeleton is changed. Meanwhile, about 30 to 50%, preferably 35 to 45% of the n-butene is skeletally isomerized into the iso-butene, and the remaining n-butene remains as 1-butene and 2-butene.

The skeletal isomerization reaction should be carried out at a high temperature of 250 to 350° C., preferably 280 to 320° C., more preferably 290 to 310° C. When the reaction is carried at a temperature of less than 250° C., is a possibility that the reaction conversion is low or the amount of iso-butene produced by skeletal isomerization is low. When the temperature is more than 350° C., the yield of the by-product is high so that there is a possibility that yield of the iso-butene is low or the inactivation occurs rapidly. Further, the skeletal isomerization catalyst used in the skeletal isomerization reaction may be a conventional acid catalyst, and preferably zeolite, aluminum phophate, tungsten oxide, most preferably a ferrierite type zeolite. On the other hand, during the skeleton isomerization process, a simple isomerization reaction proceeds at an equilibrium level, and a side reaction that partially produces 1-butene may occur.

Conventionally, among NCC(Naphtha Cracking Center) C4 mixture, C4 mixtures such as C4-raffinate generated in the naphtha pyrolysis process, in which butadiene is removed and C4 fraction produced during the catalytic cracking of heavy oil in the general oil-refining process, are used for preparing the polybutene. It is difficult to prepare polybutene containing a high amount of vinylidene and a small amount of halogen component because of 1-butene and other butene derivatives (such as n-butene) of large amounts contained in the C4 mixture. However, as shown in the present invention, when 'the isomerization and fractional distillation process' and the 'skeletal isomerization process' are performed, 1-butene and other butene derivatives are reduced or removed so that it becomes easy to prepare polybutene containing a high amount of vinylidene and a small amount of halogen component, especially high reactive polybutene.

Then, if necessary, unreacted C4 after polymerization reaction of polybutene is mixed with the reaction raw material containing a large amount of high amount iso-butene which is separated at the isomerization reactor 10 (for example, a C4 mixture having the composition of Table 3), to form a dilute C4 mixture (for example, a C4 mixture having the composition shown in Table 7 below). The dilute C4 mixture, together with polymerization catalysts, is supplied to a polybutene polymerization reactor 30, to produce polybutene through the polymerization reaction.

The production process of the polybutene will be described in more detail. In the polybutene polymerization reactor 30, the C4 mixture containing iso-butene of the composition shown in Table 7 below and the catalyst are contacted and polymerized to form a reaction product. The reaction product is subjected to a neutralizing process (not shown) for removing the catalyst for the reaction product and a refining process (not shown) for separating the reaction product without the catalyst into organic compounds and water. In a C4 stripper 40, unreacted C4 is discharged via distillation and passes through an adsorption tower 42 and then recycled back to the reactor and the remaining organic compounds are transferred to a LP (light polymer) distillation column (vacuum stripper) 50. In the LP distillation column, of the remaining organic compounds, LP is discharged and recovered through distillation, and the remainder can be obtained as polybutene.

Of the polybutene prepared, conventional polybutene in which the amount of vinylidene at the end of the double bond is less than 70 mol % can be polymerized using an aluminum trichloride catalyst, and the highly reactive polybutene having a vinylidene amount of more than 70 mol % can be polymerized using a main catalyst such as boron trifluoride and a cocatalyst of alcohol or ether. Particularly, in the case of highly reactive polybutene, the catalyst component may be introduced directly into the polybutene polymerization reactor 30 in the form of a complex comprising a main catalyst and a cocatalyst, and alternatively, the main catalyst and the cocatalyst can be directly introduced into the polybutene polymerization reactor 30, respectively. The catalyst component may be fed into a separate injection tank in the form of a complex comprising a main catalyst and a cocatalyst, and then fed to a polybutene polymerization reactor, and alternatively, the main catalyst and the cocatalyst may be individually prepared and added to separate injection tanks, respectively, and then supplied to the polybutene polymerization reactor (30). On the other hand, since the complexation reaction of the main catalyst and cocatalyst, for example, boron trifluoride and alcohol, is an exothermic reaction, to prevent the risk of catalyst decomposition and explosion, it is preferable to sufficiently remove the reaction heat to maintain the stability of the catalyst so that the complexation reaction is preferably carried out at a low temperature of 10° C. or lower, preferably 0° C. or lower, more preferably −40° C. to −10° C.

As the alcohol among the cocatalysts, primary, secondary or tertiary alcohols having 1 to 4 carbon atoms can be used. Specific examples thereof include methanol, ethanol, isopropanol, n-propanol, isobutanol and tertiary butanol and so on. As the ether among the above cocatalysts, a primary, secondary or tertiary ether having 2 to 8 carbon atoms may be used. Examples thereof include dimethyl ether, diethyl ether, diisopropyl ether, methyl propyl ether, methyl isopropyl ether, methyl ethyl ether, methyl butyl ether, methyl tertiary butyl ether, ethyl propyl ether, ethyl isopropyl ether, ethyl butyl ether, ethyl isobutyl ether and ethyl tertiary butyl ether. In addition, the above listed compounds may be mixed to be used as a cocatalyst without limitation.

With respect to the amount of the catalyst used in the polymerization reaction, it is preferable to use 0.02 to 1.0 part by weight of the main catalyst such as boron trifluoride relative to 100 parts by weight of the reaction raw material. If the amount of the catalyst is more than 1.0 part by weight based on 100 parts by weight of the reaction raw material, not only an excessively low molecular weight product is obtained but also the productivity per catalyst is lowered. If the amount of the catalyst is used in an amount less than 0.02 part by weight, the yield of polybutene to be produced may be lowered, which may also lower the economic efficiency. The polymerization reaction for producing the polybutene (particularly, highly reactive polybutene) can be carried out by a conventional method, wherein the reaction temperature is preferably maintained at −30 to 40° C., preferably −30 to 20° C., and the reaction pressure is preferably maintained at 3 kg/cm$^2$ or more so that the reaction raw material can remain in the liquid state under the reaction temperature. In the production of polybutene, the conversion of iso-butene is 70% or more, preferably 80 to 90%, and the residence time required to obtain the above-mentioned conversion is 5 to 100 minutes, which is economically advantageous. On the other hand, the polybutene produced according to the present invention has a number average molecular weight (Mn) of 300 to 5,000 and a vinylidene amount of 80 mol % or more (i.e., 80% or more with respect to the total number of double bonds). Further, according to the present invention, polybutene can be polymerized with catalytic mileage of 300 to 1200 g-polymer/g-catalyst.

Beside effectively using the iso-butene raw material, as shown in FIG. 1, the method for producing polybutene of the present invention may recycle or recirculate the unreacted C4 which is recovered from the C4 distillation column 40 by two ways to dilute iso-butene (route A and route B in FIG. 1). The unreacted C4 which is recovered from the C4 distillation column 40 includes iso-butene of 2 to 20 weight %, preferably of 5 to 15 weight %, more preferably of 8 to 12 weight %, and n-butene of 3 to 20 weight %, preferably of 5 to 15 weight %, more preferably of 8 to 12 weight %, and an example of the unreacted C4 (raw material for dilution) has the composition shown in Table 6 below.

TABLE 6

| | iso-butene | n-butane | 1-butene | C-2-butene | T-2-butene | i-butane |
|---|---|---|---|---|---|---|
| Amount (weight %) | 10.0 | 39.3 | 7.2 | 0.9 | 1.6 | 41.0 |

First, the recycling method of the unreacted C4 according to the route A will be described. All or a part of the unreacted C4 is returned to the polybutene polymerization reactor 30 to be recycled so that C4 mixture which has high concentration of iso-butene supplied from the isomerization reactor 10 to the polybutene polymerization reactor 30 can be diluted (to be a concentration suitable for polybutene polymerization) so as to facilitate polybutene polymerization. The recycling method of unreacted C4 along route B is to improve the use efficiency of iso-butene raw material (recycle). At this time, all or a part of the unreacted C4 is returned to the isomerization reactor 10 or returned so as to be mixed to the C4 mixture fed to the isomerization reactor 10. Alternatively, the unreacted C4 may be returned to the isomerization reactor 10 and the polybutene polymerization reactor 30 at the same time through the two routes.

In the recycling process of the unreacted C4 according to the route A, it is preferable that the high concentration of iso-butene isolated from the isomerization reactor is diluted such that the concentration thereof is 25 to 65 weight %, preferably 25 to 60 weight %, for example, the iso-butene may have a composition similar to that shown in Table 7 below. The reason for lowering the amount (concentration) of iso-butene in the C4 mixture by diluting iso-butene in this manner is that if the amount of iso-butene is too high, it is difficult to control the reaction heat generated during the polymerization in the polybutene polymerization reactor 30 with a heat exchanger. However, if it is excessively diluted, the amount of iso-butene in the C4 mixture becomes excessively low, making it difficult to produce polybutene having a high molecular weight, and the production yield is also too low, leading to deteriorated economic efficiency.

The unreacted C4 may include an organic substance such as alcohol or ether containing an oxygen (O) atom, a halogen acid, and the like. In order to remove them, an adsorption tower 42 filled with an adsorbent is preferably installed. Examples of the adsorbent filled in the adsorption tower 42 include calcium hydroxide ($Ca(OH)_2$), calcium oxide (CaO), calcium carbonate ($CaCO_3$), calcium chloride ($CaCl_2$), potassium hydroxide (KOH), potassium carbonate ($K_2CO_3$), potassium carbonate ($KHCO_3$), potassium chloride (KCl), sodium hydroxide (NaOH), sodium carbonate ($Na_2CO_3$), sodium hydrogencarbonate ($NaHCO_3$), solid silica, solid alumina, anion exchange resins in which amine group is attached to resin, and cation exchange resins in which a sulfone group is attached to the resin. It is preferable to use among them, calcium hydroxide, calcium oxide, calcium carbonate, calcium chloride, solid silica, solid alumina, and resins, which are insoluble in water, after adsorbing halogen ions (X–) such as fluorine ions. The adsorption tower 42 is provided with an adsorption column for removing an organic substance such as an alcohol or an ether containing oxygen (O) atoms (an oxygen-containing organic substance) and an adsorption column for removing a halogen acid, to improve removal efficiency for respective impurities and process operation efficiency.

The adsorbent particles should be appropriately sized so as to be easily applied to a tubular fixed bed reactor in which a catalyst is fixed and a reaction target material is flowed. The size (diameter) of adsorbent particles is 0.1 to 100 mm, preferably 0.5 to 100 mm, more preferably 1 to 100 mm. Fine powder particles having a diameter of less than 0.1 mm may be difficult to apply to a tubular fixed bed reactor and particles having a diameter exceeding 100 mm. may drastically reduce adsorption efficiency. The particles of the adsorbent need to be processed (molded) into a certain form. For example, the particles can be processed into a spherical shape, a cylindrical shape, a tablet shape, and the like. Among them, a spherical shape is most preferable. Of course, in the case of the Continuous Stirred-Tank Reactor (CSTR), which is a Mixed Flow Reactor (MFR) type, all types of catalysts can be applied but the fine powder remains in this reactor, so that it is not suitable as a reactor type.

In a process for preparing conventional polybutene or highly reactive polybutene (for example, highly reactive polybutene having a vinylidene amount of 70 mol % or more, preferably 80 mol % or more and a conversion of iso-butene of 85% or more), a commonly used method can be used (using an aluminum trichloride catalyst or a boron trifluoride complex catalyst, and using a C4 mixture containing iso-butene obtained by a high purity iso-butene production (separation) method as a reaction raw material). In this case, there is a disadvantage that the cost of the raw material is so high that the cost of the product rises. However, when a C4 mixture containing iso-butene obtained through the process according to the present invention is used as a reaction raw material, it is possible to produce polybutene having a quality similar to that in the case of using high-purity iso-butene, and to increase the polybutene production by 20% or more as compared with the case of using C4-raffinate or C4 fraction.

The manufacturing apparatus used in the method for producing polybutene according to the present invention includes, as shown in FIG. 1, the isomerization reactor 10 in which 1-butene in C4 mixture supplied is isomerized to 2-butene by the isomerization reaction and iso-butene and 2-butene in the C4 mixture are separated by fractional distillation, the skeletal isomerization reactor 20 to which C4 mixture containing a large amount of 2-butene separated in the isomerization reactor 10 is supplied and in which some of the n-butene is skeletally isomerized to iso-butene, and the resulting skeletal isomerization mixture is fed into the isomerization reactor 10 and recycled, and the polybutene polymerization reactor 30 in which the high concentration iso-butene separated in the isomerization reactor 10 is mixed with the unreacted C4 discharged from the C4 distillation column 40 to produce a diluted C4 mixture (reaction raw material), which is supplied together with the polymerization catalyst, followed by polymerization to produce a reaction product. The manufacturing apparatus further includes the C4 distillation column 40 for discharging and recovering the unreacted C4 by distilling among the unreacted C4 and the residual organic compounds which are from the distillation of the reaction products, the adsorption tower 42 equipped with adsorbents for removing the organic substances and halogen acid contained in the unreacted C4 before feeding the unreacted C4 discharged out of the C4 distillation column 40 to the isomerization reactor 10 and/or the polybutene polymerization reactor 30, for the recycling unreacted C4, and the LP distillation tower for discharging LP (light polymer) among the residual organic compounds supplied from the C4 distillation column 40 to obtain the polybutene.

The effect obtained by increasing the iso-butene amount in the C4 mixture (reaction raw material) according to the method of the present invention is not limited to the production of polybutene. Even in the production of the above-mentioned IIR (isobutylene isoprene rubber) used in automotive tires, sealants, etc., ethyleneblycol mono-t-butyl ether (ETB), DETB (diethylene glycol mono-t-butyl ether) which is a raw material for detergent for electronics, paint, coating, etc., and DIB (diiso-butene) which is available for a variety of uses in the chemical industry, the use of increasing amounts of iso-butene can results in increasing product amount and production efficiency. Accordingly, the present invention provides a method for increasing the amount of iso-butene to be used, comprising the steps of supplying C4 mixture to the isomerization reactor in which 1-buten is isomerized into 2-butene by the hydrogen isomerization reaction using an isomerization catalyst in the isomerization region of the isomerization reactor and iso-butene and 2-butene are separated by fractional distillation in the fractional distillation zone of the isomerization reactor; of supplying C4 mixture containing 2-butene separated at the isomerization reactor to the skeletal isomerization reactor in a part of n-butene is skeletally isomerized into iso-butene by a skeletal isomerization reaction using a skeletal isomerization catalyst and the skeletally isomerized mixture is fed to the isomerization reactor and recycled; and of obtaining the iso-butene raw material containing the increased amount of iso-butene from the fractional distillation zone.

Hereinafter, the present invention will be described in more detail with reference to specific examples. The examples below are only to illustrate the present invention, and the present invention is not limited to the examples below.

[Example 1] Measurement of Iso-Butene Amount in Reaction Material

Of the C4 mixture the C4 raffinate (raw material) from which the butadiene is removed (the composition as shown in Table 1) was fed into an isomerization reactor (column) which is filled with 200 g of catalyst, alumina support being impregnated with platinum (0.5%). Then, isomerization and fractional distillation were carried out at a weight hour space velocity (WHSV) of 1 h−1, a temperature of 60° C. and a pressure of 8 bar so that a C4 mixture having the composition shown in Table 3 was discharged through the upper part of the reactor and a C4 mixture having the composition shown in Table 4 was discharged through the lower part of the reactor. Subsequently, a C4 mixture of the composition of Table 4 come out to the lower part of the isomerization reactor was fed into the upper part of the skeletal isomerization reactor filled with 200 g of zeolite catalyst and skeletal isomerization was carried out at a WHSV of 5 h−1, a temperature of 300° C. and a pressure of 2 bar. After completing the skeletal isomerization reaction, a part of the unreacted C4 discharged and recovered from the C4 distillation column, together with the C4 mixture having the composition shown in Table 5 which was discharged through the lower portion of the skeletal isomerization reactor, was supplied to the isomerization reactor, and then a continuous process was performed. It could be seen that amount of iso-butene contained in the C4 mixture supplied to the polybutene polymerization reactor, that is, the reaction raw material having the composition as shown in Table 1, was increased from 465 g to 593 g per kg.

[Example 2] Measurement of Iso-Butene Amount in Reaction Material

The same procedures as in Example 1 were carried out except for using C4 fractions (material having composition as in Table 2) produced during the catalytic cracking of heavy oil during the refining process. The amount of iso-butene in 1 kg of the reaction raw material having the composition shown in Table 2 was measured so that it was found that the amount was increased from 354 g to 480 g.

[Example 3] Polymerization of Highly Reactive Polybutene Having Molecular Weight of 1,000

To a stainless pressure reactor (polybutene polymerization reactor) with a cooling device, reaction materials (C4 mixture) having the composition shown in Table 7 below and isopropyl alcohol/boron trifluoride complex catalyst (1.5 moles) of 0.19 parts by weight with respect to 100 parts by weight of the reaction raw materials, were continuously injected. The reaction temperature was maintained at −18° C. and the reaction pressure was maintained at 3 kg/cm² or more so as to maintain the liquid phase of the reaction raw materials, and the average residence time was 30 minutes. After 180 minutes, the reaction product was passed through a neutralization tank which was treated with a 5 weight % caustic soda solution and then passed through a water bath washing the reaction product with water by using the liquid-phase layer separation principle. Subsequently, the reaction product is transferred to the C4 distillation column at 160° C. and atmospheric pressure to remove unreacted C4, and some of the unreacted C4 removed is recycled to the polymerization reactor inlet to be the iso-butene concentration of Table 7 below. And the remainder was introduced into the isomerization reactor (column). On the other hand, the reaction product discharged through the lower part of the C4 distillation column was transferred to a LP (Light Polymer) distillation column at a temperature of 220° C. and a pressure of 5 mmHg. Then, LP was removed through the upper part of the LP distillation column and polybutene was obtained through the lower part of the LP distillation column. The molecular weight of the prepared polybutene was measured by GPC (Gel Permeation Chromatography) and analyzed by C13-NMR. The results are shown in Table 8 and the conversion of iso-butene was 95% and the amount of vinylidene was 90 mol (Mn=970, PD=1.32). The amount of polybutene in Table 8 was obtained by treating 1 kg of raw materials.

[Example 4] Polymerization of Highly Reactive Polybutene Having Molecular Weight of 1,300

To a stainless pressure reactor (polybutene polymerization reactor) with a cooling device, reaction materials (C4 mixture) having the composition shown in Table 7 below and isopropyl alcohol/boron trifluoride complex catalyst (1.45 moles) of 0.19 parts by weight with respect to 100 parts by weight of the reaction raw materials, were continuously injected. The procedure of Example 3 was repeated except that the reaction temperature was set to −23° C., to obtain product. The product was analyzed, and the results are shown in Table 8 and the conversion of iso-butene was 94% and the amount of vinylidene was 90 mol % (Mn=1360, PD=1.44). Similarly, the amount of polybutene produced in Table 8 is obtained by treating 1 kg of the raw material.

[Example 5] Polymerization of Highly Reactive Polybutene Having Molecular Weight of 2,300

To a stainless pressure reactor (polybutene polymerization reactor) with a cooling device, reaction materials (C4 mixture) having the composition shown in Table 7 below and isopropyl alcohol/boron trifluoride complex catalyst (1.35 moles) of 0.15 parts by weight with respect to 100 parts by weight of the reaction raw materials, were continuously injected. The procedure of Example 3 was repeated except that the reaction temperature was set to −28° C., to obtain product. The product was analyzed, and the results are shown in Table 8 and the conversion of iso-butene was 93% and the amount of vinylidene was 89 mol % (Mn=2350, PD=1.61). Similarly, the amount of polybutene produced in Table 8 is obtained by treating 1 kg of the raw material.

TABLE 7

|  | iso-butene | n-butane | 1-butene | C-2-butene | T-2-butene | i-butane |
|---|---|---|---|---|---|---|
| Amount (weight %) | 53.0 | 17.2 | 4.4 | 4.0 | 3.3 | 18.1 |

TABLE 8

| | Catalytic mileage | Vinylidene amount (mole %) | Product yield (polybutene/raw material, %) | Production amount of polybutene (g) |
|---|---|---|---|---|
| Example 3 | 608 | 90 | 56.8 | 568 |
| Example 4 | 683 | 90 | 56.5 | 565 |
| Example 5 | 832 | 89 | 55.3 | 553 |
| Comparative Example 1 | 276 | 85 | 38.1 | 381 |
| Comparative Example 2 | 173 | 83 | 21.0 | 210 |

[Comparative Example 1] Polymerization of Highly Reactive Polybutene Having Molecular Weight of 1,000

To a stainless pressure reactor (polybutene polymerization reactor) with a cooling device, reaction materials (C4 mixture) having the composition shown in Table 1 below and isopropyl alcohol/boron trifluoride complex catalyst (1.4 moles) of 0.37 parts by weight with respect to 100 parts by weight of the reaction raw materials, were continuously injected. The reaction temperature was maintained at −17° C. Polybutene was obtained in the same manner as in Example 1 except that the unreacted C4 removed from the C4 distillation column was not recycled. The results of analysis of the produced polybutene are shown in Table 8, and the conversion of iso-butene was 84% and the amount of vinylidene was 85 mol % (Mn=980, PD=1.31).

[Comparative Example 2] Polymerization of Highly Reactive Polybutene Having Molecular Weight of 1,000

To a stainless pressure reactor (polybutene polymerization reactor) with a cooling device, reaction materials (C4 mixture) having the composition shown in Table 2 below and isopropyl alcohol/boron trifluoride complex catalyst (1.4 moles) of 0.45 parts by weight with respect to 100 parts by weight of the reaction raw materials, were continuously injected. The reaction temperature was maintained at −16° C. Polybutene was obtained in the same manner as in Example 1 except that the unreacted C4 removed from the C4 distillation column was not recycled. The results of analysis of the produced polybutene are shown in Table 8, and the conversion of iso-butene was 67% and the amount of vinylidene was 83 mol % (Mn=960, PD=1.35).

As shown in the above Examples and Comparative Examples, when the process system according to the present invention (isomerization and fractionation process, skeleton isomerization process and recycle of unreacted C4) is used, it can be seen that not only the amount of iso-butene per unit raw material and the amount of iso-butene itself are increased but also the amount of polybutene to be polymerized is greatly increased. In addition, the amount of the catalyst used in the production of the product (polybutene) is reduced more than two times, whereby the production cost is remarkably reduced, thereby increasing the amount of polybutene that can be produced in a single plant. Also, it can be seen that the vinylidene amount, which is an important physical property of the highly reactive polybutene, is also high.

The invention claimed is:

1. A method for preparing polybutene, comprising the steps of:

supplying a C4 mixture to an isomerization reactor in which (i) 1-butene is isomerized into 2-butene by a hydrogen isomerization reaction using an isomerization catalyst in an isomerization zone of the isomerization reactor and (ii) iso-butene and 2-butene are separated by fractional distillation in a fractional distillation zone;

supplying a C4 mixture containing 2-butene which is separated in the isomerization reactor to a skeletal isomerization reactor, in which a part of normal-butene is skeletal isomerized into iso-butene by a skeletal isomerization reaction using a skeletal isomerization catalyst, and the obtained skeletal isomerization mixture is supplied and recycled to the isomerization reactor;

supplying (i) a raw material containing the iso-butene of high concentration and which is separated from the isomerization reactor and (ii) a polymerization catalyst to a polybutene polymerization reactor and thereby producing polybutene by a polymerization reaction; and after the polymerization reaction, recycling whole or a part of unreacted C4 of the polymerization reaction to the isomerization reactor.

2. The method of claim 1, wherein the polymerization catalyst comprises a main catalyst, a cocatalyst and an auxiliary cocatalyst, and the main catalyst is a Lewis acid selected from the group consisting of boron trifluoride, boron trichloride, aluminum trichloride and zinc chloride, and the cocatalyst is selected from the group consisting of water and an alcohol compound, and the auxiliary cocatalyst is an alkyl ether compound.

3. The method of claim 1, wherein, after the polybutene polymerization reaction, the iso-butene amount in the unreacted C4 is 2 to 20 weight %.

4. The method of claim 1, wherein the polybutene is polymerized with a catalyst mileage of 300 to 1200 g-polymer/g-catalyst.

5. The method of claim 1, wherein the polybutene is a conventional polybutene having 70 mol % or less of vinylidene in which a double bond is located at a terminal of the polybutene.

6. The method of claim 1, wherein the polybutene is a highly reactive polybutene having more than 70 mol % of vinylidene in which a double bond is located at a terminal of the polybutene, and whose molecular weight is from 300 to 5,000.

7. The method of claim 1, wherein the polymerization reaction is carried out at a temperature of −30 to 40° C. and at a pressure of 3 kg/cm$_2$ or more for a residence time of 5 to 100 minutes.

8. The method of claim 1, further comprising a step of removing an oxygen-containing organic substance and a halogen acid contained in the unreacted C4 of the polymerization reaction by using an impurity adsorption tower equipped with an adsorbent.

9. The method of claim 8, wherein the adsorbent is a compound selected from the group consisting of calcium hydroxide (Ca(OH)$_2$), calcium oxide (CaO), calcium carbonate (CaCO$_3$), calcium chloride (CaCl$_2$), potassium hydroxide (KOH), potassium carbonate (K$_2$CO$_3$), potassium bicarbonate (KHCO$_3$), potassium chloride (KCl), sodium hydroxide (NaOH), sodium carbonate (Na$_2$CO$_3$), sodium hydrogencarbonate (NaHCO$_3$), solid silica, solid alumina, zeolite, anion exchange resins in which amine group is attached to resin, and cation exchange resins in which a sulfone group is attached to the resin.

10. The method of claim 8, wherein the adsorption tower is provided with an adsorption column for removing oxygen-containing organic substance contained in the unreacted C4 and an adsorption column for removing halogen acid contained in the unreacted C4.

11. An apparatus for preparing polybutene, comprising:
an isomerization reactor to which a C4 mixture is supplied and in which (i) 1-butene of the C4 mixture is isomerized into 2-butene by a hydrogen isomerization reaction and (ii) iso-butene and 2-butene of the C4 mixture are separated by fractional distillation;
a skeletal isomerization reactor to which a C4 mixture containing 2-butene separated in the isomerization reactor is supplied and in which a part of normal-butene is skeletal isomerized into iso-butene to obtain a skeletal isomerization mixture, and the obtained skeletal isomerization mixture is supplied and recycled to the isomerization reactor;
and a polybutene polymerization reactor to which (i) a raw material containing high concentration of iso-butene separated from the isomerization reactor and (ii) a polymerization catalyst are supplied and polymerized, thereby producing a reaction product;
wherein a whole or a part of unreacted C4 of the polymerization reaction is recycled in the isomerization reactor.

12. The apparatus of claim 11, further comprising:
a C4 distillation column for distilling the reaction product to separate unreacted C4 and residual organic compounds and for discharging the unreacted C4;
an adsorption tower provided with an adsorbent for removing organic substances and halogen acid which are contained in the unreacted C4, before returning the unreacted C4 which is discharged from the C4 distillation column to the isomerization reactor and/or the polybutene polymerization reactor;
and a LP distillation column for discharging a light polymer among the residual organic compounds supplied from the C4 distillation column, thereby obtaining polybutene.

* * * * *